US00RE35330E

United States Patent [19]

Malone et al.

[11] E Patent Number: Re. 35,330

[45] Reissued Date of Patent: Sep. 17, 1996

[54] HOT TIP CATHETER ASSEMBLY

[75] Inventors: David G. Malone, Mission; James L. Vacek, Shawnee Mission, both of Kans.; G. Scott Smith, Colorado Springs, Colo.

[73] Assignee: University of Kansas Medical Center, Kansas City, Kans.

[21] Appl. No.: 136,414

[22] Filed: Oct. 13, 1993

Related U.S. Patent Documents

Reissue of:

[64] Patent No.: 5,057,105
Issued: Oct. 15, 1991
Appl. No.: 571,212
Filed: Aug. 23, 1990

U.S. Applications:

[63] Continuation-in-part of Ser. No. 399,773, Aug. 28, 1989, abandoned.

[51] Int. Cl.[6] ..... A61B 17/38

[52] U.S. Cl. ..... 606/28; 606/31

[58] Field of Search ..... 606/27–29, 31, 606/11, 12, 38–40; 607/96, 99, 102; 219/241, 494

[56] References Cited

U.S. PATENT DOCUMENTS

| | | |
|---|---|---|
| 3,369,750 | 2/1968 | Davis . |
| 3,595,238 | 7/1971 | Sheikmana . |
| 3,662,151 | 5/1972 | Haffey . |
| 3,692,986 | 9/1972 | Nienstaedt et al. . |
| 4,022,214 | 5/1977 | Schulze et al. . |
| 4,182,183 | 1/1980 | Funk et al. . |
| 4,209,017 | 6/1980 | Shaw . |
| 4,275,439 | 6/1981 | Kuwata . |
| 4,411,266 | 10/1983 | Cosman . |
| 4,449,528 | 5/1984 | Auth et al. . |
| 4,539,987 | 9/1985 | Nath et al. . |
| 4,582,057 | 4/1986 | Auth et al. . |
| 4,592,353 | 6/1986 | Daikuzono . |
| 4,643,186 | 2/1987 | Rosen et al. . |
| 4,646,737 | 3/1987 | Hussein et al. . |
| 4,654,024 | 3/1987 | Crittenden et al. . |
| 4,662,368 | 5/1987 | Hussein et al. . |
| 4,669,467 | 6/1987 | Willett et al. . |
| 4,672,962 | 6/1987 | Hershenson . |
| 4,691,703 | 9/1987 | Auth et al. . |
| 4,695,709 | 9/1987 | Sachs et al. . |
| 4,735,201 | 4/1988 | O'Reilly . |
| 4,747,405 | 5/1988 | Leckrone . |
| 4,748,979 | 6/1988 | Hershenson . |
| 4,760,845 | 8/1988 | Kovalcheck . |
| 4,765,330 | 8/1988 | Bach . |
| 4,773,413 | 9/1988 | Hussein et al. . |
| 4,776,334 | 10/1988 | Prionas . |
| 4,796,622 | 1/1989 | Lu et al. . |
| 4,860,744 | 8/1989 | Johnson et al. . |
| 4,899,741 | 2/1990 | Bentley et al. . |
| 4,907,589 | 3/1990 | Cosman . |
| 4,955,377 | 9/1990 | Lennox et al. . |
| 4,966,597 | 10/1990 | Cosman . |
| 5,006,119 | 4/1991 | Acker et al. . |
| 5,035,694 | 7/1991 | Kasprzyk et al. . |

FOREIGN PATENT DOCUMENTS

| | | | |
|---|---|---|---|
| 3541960 | 7/1986 | Germany | A61B 17/38 |
| 2138297 | 10/1984 | United Kingdom | A61B 17/40 |

*Primary Examiner*—Lee S. Cohen
*Attorney, Agent, or Firm*—Ryan, Maki, Mann & Hohenfeldt

[57] ABSTRACT

A hot tip catheter assembly is disclosed which resolves atherosclerotic plaque buildup in vivo. The catheter has a heater, a cap, a thermocouple, power leads, thermocouple leads, and a central distal lumen to position the catheter within the artery. The catheter tip has a thin, non-adhesive coating of a hard, heat-conducting material. The thermocouple is used to continuously evaluate the temperature at the tip of the catheter, and the temperature is then regulated by a computer-controlled feedback system. The catheter can completely melt the buildup without damage to the artery by direct contact with the plaque, without use of balloon catheter angioplasty.

25 Claims, 4 Drawing Sheets

HOT TIP CATHETER ASSEMBLY

Matter enclosed in heavy brackets [ ] appears in the original patent but forms no part of this reissue specification; matter printed in italics indicates the additions made by reissue.

This application is a continuation-in-part of Ser. No. 07/399,773; filed Aug. 28, 1989, now abandoned.

BACKGROUND OF THE INVENTION

1. Field of the Invention

The present invention is concerned with a system for resolving atherosclerotic plaque build-up in vivo. More particularly, the invention hereof involves a hot tip catheter assembly and technique for temperature control removal of arterial plaque.

2. Description of the Prior Art

Coronary artery disease occurs when arteries which supply oxygen-rich blood to the heart are narrowed (partially blocked) by a build up of fatty and fibrous substances known as atherosclerotic plaque. Arteries are composed of three layers. The innermost layer is the intima, the middle layer is the muscularis, and the outermost layer is the adventitia. The atherosclerotic plaque is deposited directly underneath the intima. The plaque can build up on coronary as well as peripheral arteries.

Various conventional methods are currently used for opening arteries which are constricted by atherosclerotic plaque, and several accomplish this by compression or removal of the plaque which results in residual sites of injury which predisposes to recurrent occlusion. These methods are generally seen as alternatives to coronary artery bypass procedures which are expensive and traumatic in terms of patient morbidity. One of the most commonly used methods is percutaneous transluminal balloon dilatation (angioplasty) which reduces the blockage by dilatation of the lumen of the artery, which reforms and compresses atherosclerotic plaque. Another method is the use of implantable stents in cases where the arteries have failed to remain patent after balloon angioplasty. Atherectomy devices are used to physically cut through the atherosclerotic plaque and remove it from the artery. Laser angioplasty is also available wherein a channel is created through the arteries by heating or melting the plaque using a laser. Other non-laser devices have been developed which also soften or melt plaque using various thermal means.

Balloon angioplasty is not always effective, however, especially when the plaque has hardened due to the presence of a high concentration of calcium in the plaque. Further, if the lumen of the artery is mostly or completely constricted, balloon angioplasty is not feasible as the balloon catheter cannot be placed within the opening of the blockage.

The angioplasty devices which are currently used to soften or melt the atherosclerotic plaque have several drawbacks. These devices often cause damage to the interior walls of the arteries by misdirecting the thermal energy used, focusing it on the arterial wall rather than the plaque. Damage can also be caused by a failure to accurately and effectively regulate and maintain the temperature of the thermal energy used. If the temperature gets too high, a hole can be burned through the wall of the artery. No effective system for precisely regulating temperature at the tip of a thermal ablating device are available.

Furthermore, conventional thermal devices often have problems being cooled by the surrounding tissue with sufficient speed, generally due to the relatively high thermal mass of the catheters. Current leakage has been another problem with prior thermal devices, which may result in lethal cardiac arrhythmias. An additional problem with prior thermal devices is the formation of char from themally damaged debris on the top of the heated cap, which may cause adhesion of the catheter tip to the vessel wall.

SUMMARY OF THE INVENTION

In response to these problems, the device of the present invention provides a catheter having a specific heating element, a heat-transferring metallic cap; a thermocouple, power leads, thermocouple leads, a central distal lumen for positioning the tip of the catheter over a guide wire and/or injecting contrast dye and/or performing pressure measurements, and a computer-based control system. The catheter tip can be positioned over a guide wire which has been placed within the artery proximate to the atherosclerotic plaque blockage.

The heater element is composed of a semiconductor, which must be modified to fit within the tight confines of a coronary artery. While it can be made using any of several suitable semiconductors, in one embodiment the semiconductor is a package containing three avalanche diodes connected in series.

The control system is comprised of specifically designed and integrated computer hardware and software. The goal of the control system is to keep the catheter tip within 10° C. of the desired temperature, and below 180° C. The thermocouple is used to continuously evaluate the temperature at the catheter tip, and the tip is brought to its proper temperature by the computer-controlled feedback system which determines the amount of voltage which must be provided by the power supply to the catheter tip. In this manner, the proper catheter tip temperature is constantly maintained in order to minimize the risk of any damage to the muscularis while preferentially ablating the atherosclerotic elements of the plaque.

The catheter tip, when properly positioned within the artery, melts the atherosclerotic plaque by direct conduction of heat. The plaque can be melted so completely that there is no need to follow this procedure with balloon catheter angioplasty. The site of thermal ablation is less likely to result in reocclusion rather than if other methods which leave a focus of arterial wall injury are utilized. The catheter tip is coated with a thin, heat-conducting substance such as Teflon, a silicon compound, or a ceramic substance which promotes free movement of the catheter within the vessel and avoids build-up of char on the catheter tip and adhesion of the heating element of the vessel.

Accordingly, it is the primary object of the present invention to provide a device to be used inside of an artery for removing obstructions therein, such as atherosclerotic plaque, without regard to the degree of blockage existing.

It is another object of the invention to provide a device as described above, wherein the atherosclerotic plaque in arteries is removed by melting.

It is a further object of the present invention to provide a device as described above, wherein the atherosclerotic plaque can be melted with a relatively low rate of perforation of the walls of the arteries.

It is yet another object of the present invention to provide a device as described above, wherein the temperature of the tip of the catheter is continuously monitored and regulated and can be maintained at the exact temperature necessary for the angioplasty process.

It is still another object of the present invention to provide a device as described above, wherein the monitoring and regulating of the catheter tip temperature is controlled by a thermocouple and a minicomputer feedback control system.

It is another object of the present invention to provide a device as described above, wherein the catheter tip is coated with a thin, hard conductive, but non-adhesive material to avoid debris build-up on the catheter tip and promote catheter mobility within the vessel.

It is a still further object of the present invention to provide a device as described above, wherein the catheter tip is rapidly and efficiently heated by using avalanche or zener diodes.

It is a further object of the present invention to provide a device as described above, wherein the catheter assembly is inexpensive, easy to work with, sturdy and uses materials readily available.

It is still another object of the present invention to provide a device as described above, wherein the minicomputer feedback system provides for automatic shutoff at the tip in any emergent situation.

It is yet a further object of the present invention to provide a device as described above, wherein a minimal amount of current leakage occurs.

Other objects and advantages of this invention will become apparent from the following description taken in connection with the accompanying drawings, wherein is set forth by way of illustration and example, an embodiment of this invention.

DESCRIPTION OF THE PREFERRED EMBODIMENT

Figure 1:
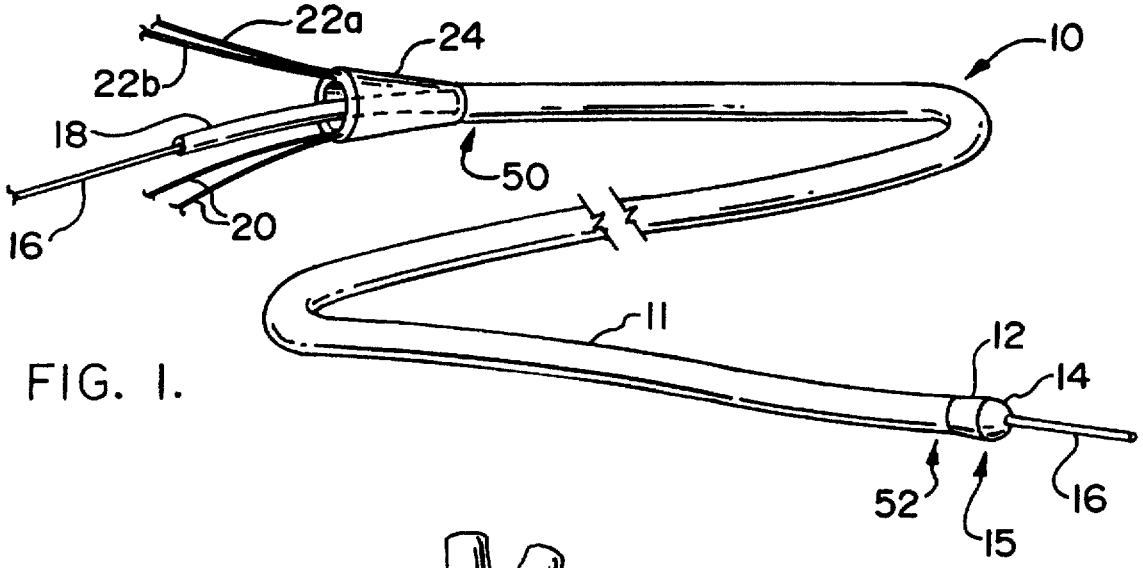
FIG. 1 is a perspective view of the hot tip catheter assembly, the minicomputer control system not being shown.

FIG. 1 depicts a hot tip catheter assembly, generally referred to as 8, having a body 10 and a catheter tip 15 which is composed of a heater element 12 and a catheter cap 14. The cap 14 is preferably elliptical in shape. The tip 15 is adjacent a distal end 52 of the catheter body 10. A central opening or guide wire lumen 17 extends longitudinally throughout the catheter body 10, and the catheter tip 15. A guide wire port 18 extends from a proximal end 50 of the catheter 10 and is designed to receive a guide wire 16. The guide wire 16 extends from the port 18 through the central opening 17 beyond the tip 15. Power leads 22a and 22b extend longitudinally through a fitting 24 and the body 10, and are connected to the heater element 12. In a similar manner, thermocouple leads 20 are connected to the heating element 12 and extend longitudinally through the body 10 and the fitting 24. A catheter sheath 11 extends from the fitting 24 to the cap 14. A thin layer of non-adhesive coating surrounds the catheter sheath 1i from the cap 14 to the proximal end 50, and is depicted in FIG. 4.

Figure 2:
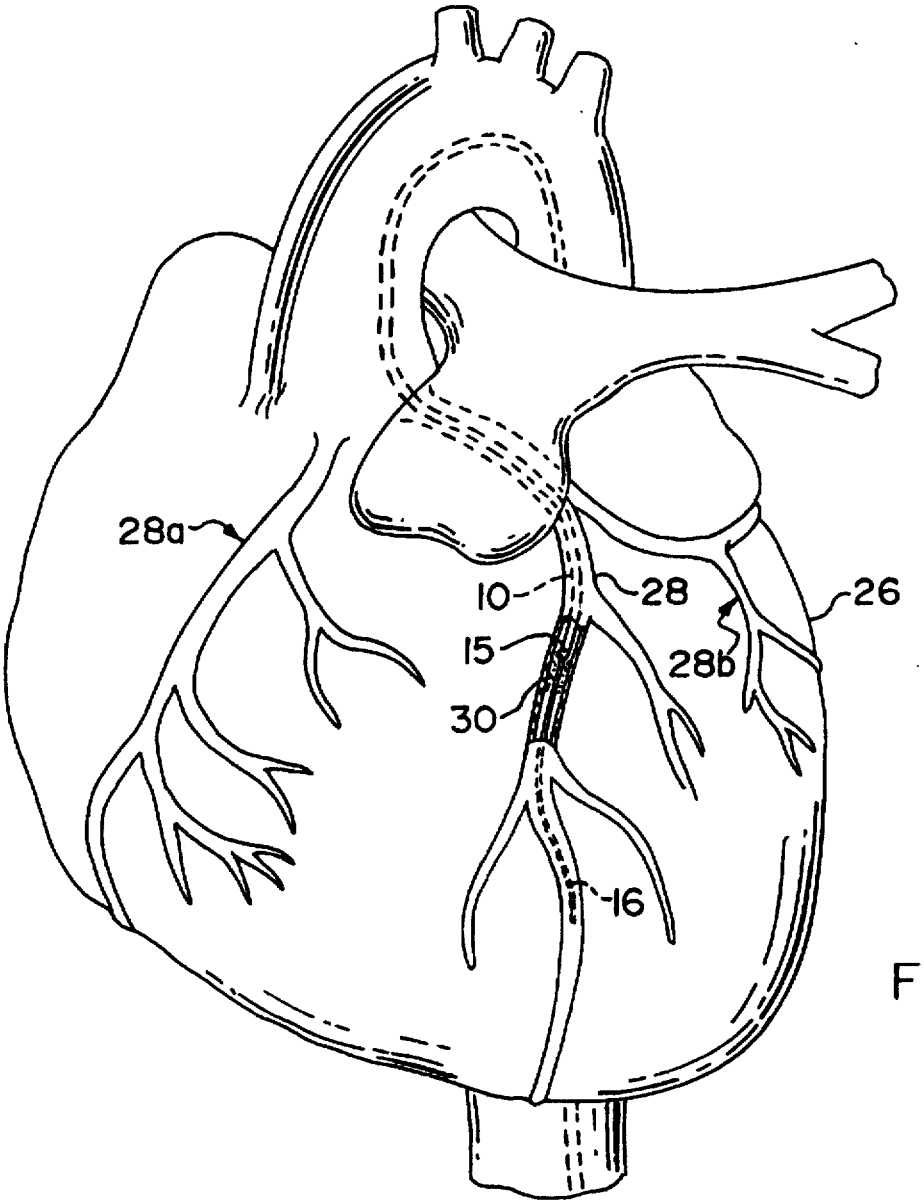
FIG. 2 is a perspective view depicting the catheter of FIG. 1 positioned within a coronary artery having atherosclerotic plaque buildup, with a portion of the artery broken away to show the catheter tip approaching the blockage, the broken lines representing the catheter body.

FIG. 2 shows the catheter assembly 8 positioned within a coronary artery 28 proximate to a buildup of atherosclerotic plaque 30. The guide wire 16 extends beyond the catheter cap 14 and through the plaque blockage 30. The catheter and guide wire assembly 16 may be positioned at any of several points in this vessel 28 or other coronary arteries 28a and 28b or the branches thereof depending on the site of atherosclerotic obstruction.

Figure 3:
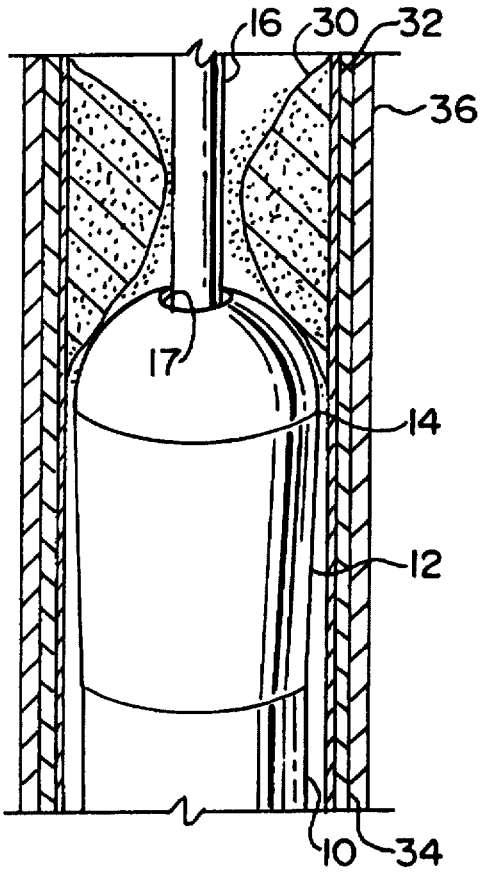
FIG. 3 is an enlarged perspective view of the catheter tip being led by the guide wire within an artery which is shown in cross section, proximate to the build-up of atherosclerotic plaque.
Figure 4:
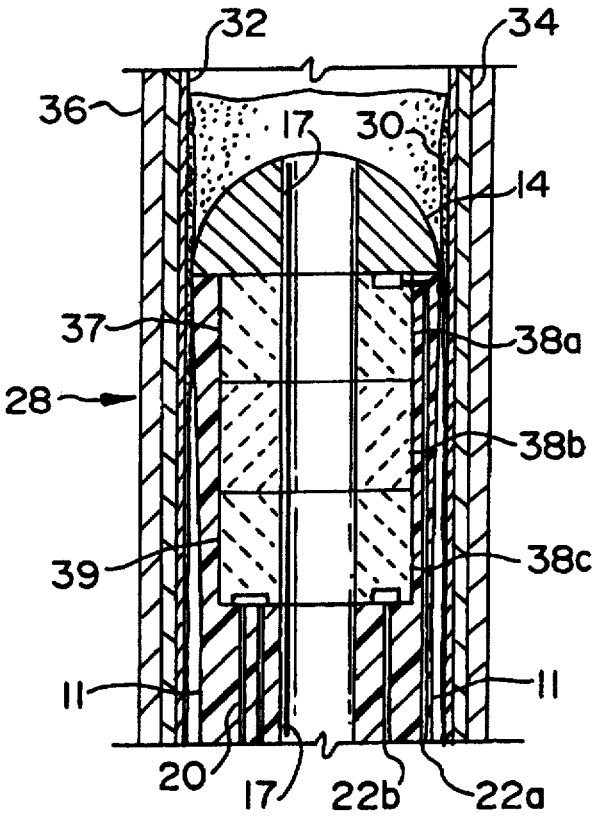
FIG. 4 is an enlarged cross-sectional view of the catheter as in FIG. 3, with a majority of the atherosclerotic plaque resolved.

FIGS. 3 and 4 show an enlarged detail view of the catheter tip 15 positioned within an artery proximate to the atherosclerotic plaque buildup 30. FIG. 4 shows the buildup 30 after it has been resolved by the angioplasty catheter assembly 8. The three layers of the artery wall are depicted and are the intima 32, the muscularis 34, and the adventitia 36.

Figure 5:
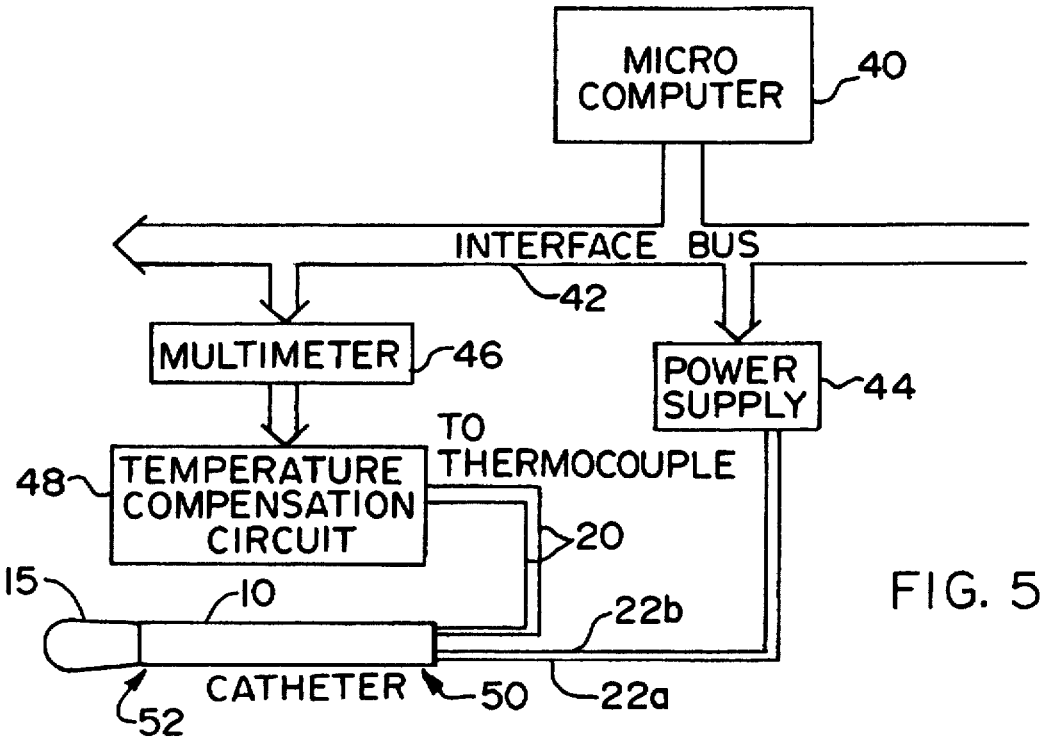
FIG. 5 is a schematic diagram of the power supply and microcomputer control assembly connected to the hot tip catheter assembly.

Referring again to FIG. 4, the heater element 12 is comprised, in one embodiment, of triple-stacked avalanche or zener diodes 38a, 38b and 38c. The cap 14 is connected to end 37 of the diode package 38. The catheter sheath 11 extends from the cap 14 to the proximal end 50 and peripherally surrounds the diode package 38. The non-adhesive coating 25 is a thin, hard conductive material. This material can be any suitable substance, but is preferably Teflon, a silicon compound, or a ceramic material. The guide wire opening 17 extends throughout the cap 14 and the diode package 38. The power leads 22a and 22b are attached to ends 37 and 39, respectively, of the diode package 38, with the positive power lead 22b attached to the cathode 39 of the diode package 38, and the negative power lead 22a attached to the anode 37 of the diode package 38. As seen in FIG. 5, the leads 22a and 22b connects the diode package 38 to a power supply 44. Thermocouple leads 20 connect end 39 of the diode package 38 with the temperature compensation circuit 48.

Referring now to FIG. 5, the minicomputer feedback system is composed of the temperature compensation circuit 48 (optional) connected to the catheter tip 15 by the thermocouple leads 20, a multimeter 46, an interface bus 42, a minicomputer 40, and the power supply 44 which is connected to the catheter tip 15 by the power leads 22a and 22b.

As discussed above, the heater element 12 of the preferred embodiment is composed of a semiconductor package 38 of three avalanche or zener diodes 38a, 38b and 38c in series. A diode is a single P-layer/N-layer interface. The N-layer contains minute amounts of electron rich materials such as phosphorus, arsenic, antimony or bismuth. The P-layer contains minute amounts of materials with only three electrons in the valence band such as boron, aluminum or gallium. When p-type and N-type materials are placed together forming a junction, electrons from the negative region diffuse across the junction into the P region. In a similar fashion, "holes" from the P region diffuse along the concentration gradient from the P region to the N region. This sets up an electric field with a barrier voltage across the junction preventing any further diffusion across the junction in the equilibrium state. An external electric field can be applied to the junction by applying an external voltage. This external voltage can have two polarities. If the positive external voltage is applied to the P-type material and the negative voltage to the N-type material, flow of electrons will occur from the negative to the positive material. As conventional current flows uses hole conduction, the conventional current flows in the opposite direction of electron flow. With current flow from the P-type layer to the N-type layer material as above, the junction is in the forward biased condition and the barrier voltage is lowered.

If the junction is reverse biased with the positive exterior voltage applied to the N-type material and the negative voltage applied to the P-P-type material, the external applied voltage is added to the internal barrier voltage. This requires more energetic electrons to cross the heightened energy barrier in the reverse biased case. Quantum mechanics show the existence of a small population of electrons with sufficient energy to cross the energy gap from the P to the N direction. This is called Is, the saturation current, and it is a small negative current. If a sufficiently large reverse biasing voltage is applied it creates a large electric field across the junction. As an electron with sufficient energy to bridge the gap enters from the anode it is accelerated by the electric field in the junction, thereby gaining more energy. Invariably this electron crossing the junction collides with other bound electrons in the lattice of the junction. If the collision is energetic enough it will dislodge other electrons from the lattice and these dislodged electrons will also be accelerated by the electric field and will collide with other electrons bound to the lattice causing large reverse currents known as breakdown in the avalanche fashion. The large reverse voltage needed to cause this event is called the avalanche breakdown voltage. Another phenomenon called zener breakdown also occurs.

In a simplified fashion, zener breakdown occurs when an electron in the P-layer side with energy below that needed to cross the junctional energy barrier appears on the N-layer side This is called "tunneling", as it appears as if the electron has tunneled under the energy gap, and it results in a negative current called Iz. Thus, the breakdown voltage for any diode is either the zener or the avalanche breakdown voltage and the breakdown current is composed of both the zener and avalanche current. If voltages larger than the avalanche and zener breakdown voltages are applied to the junction, an increased amount of heat is generated. This heat generation causes the thermal generation of hole electron pairs far in excess of that caused by doping the semiconductors with P and N-type material, and the semiconductor acts as if it were pure silicon.

The heater element 12 of the catheter assembly 8 uses a diode package 38 of three 68 volt avalanche diodes 38a, 38b and 38c connected in series. These diodes 38a, 38b and 38c are all reverse biased and the electric field of the reverse biased junctions adds to the resistance of the diode package 38. At the avalanche breakdown voltage the device behaves as a conventional diode. However, when a larger voltage is applied and the junctions are heated sufficiently by the external voltage, the overwhelming majority of hole-electron pairs are from thermal generation. At this point, the seimconductor package 38 is no longer behaving as three diodes in series, but rather as one single piece of pure silicon. Therefore, the use of avalanche diodes is not essential to the success of the catheter assembly 8, but it does provide more rapid heating. Similarly, although the temperature of avalanche diodes can generally be predicted by their current-voltage characteristics, it is not the case in this invention when the junction is at high temperatures and the diodes are not behaving as conventional diodes, thus necessitating the use of a temperature measuring device in the catheter tip 15, which is composed of the thermocouple leads 20 and the temperature compensation circuit 48.

In this embodiment, the positive power lead 22b is welded with silver or other metals to the cathode 39 of the diode package 38, and the negative power leads 22a is welded to the anode 37 of the diode package 38. The cathode 39 of the diode 38 also has type J thermocouple leads 20 welded to it. The positive power leads 22b/cathode 39/thermocouple lead 20 package is bonded with high temperature silicon adhesive into the distal end 52 of the catheter sheath 11. A silver, stainless steel or brass, elliptically shaped cap 14 with a guide wire opening 17 is welded to the negative power lead 22a/anode 37 of the diode package 38 and is coated with a layer of material having thermal and electrical characteristics similar to ceramic. The catheter sheath 11 has four lumens, two lumens contain the power leads 22a and 22b, one lumen contains a single thermocouple lead 20, the other thermocouple lead passes with the low voltage power lead, and the last lumen contains is the central guide wire opening 17 for the guide wire 16 and contrast dye. Opening 17 can also be used for a saline solution when such is needed to cool the catheter tip 15.

The control segment of the system is composed of hardware and software. The power supply 44, multimeter 46, and interface card 42 are all commercially available devices. These components together with a computer 40 such as the IBM compatible computer of the preferred embodiment form the hardware segment of the control system for the catheter assembly 8. The thermocouple 20 and multimeter 46 measure catheter tip 15 temperature, and the programmable power supply 44 provides the energy needed to heat the tip 15. These devices are connected to the microcomputer 40 by an interface bus 42, and the events of the system 8 are controlled by a specifically-designed software program. The software catheter assembly 8 models its mathematical and thermal characteristics. The goal of the control system is to keep the catheter tip 15 within 10° C. of the desired temperature and below 180° C. This is accomplished as shown in the flow diagram of FIG. 6. and is described as follows. The operator inputs a desired tip temperature and the system compares the temperature of the catheter tip 15 as measured by the thermocouple 20 to the desired temperature; this difference is called the error temperature. The system continually cycles at a frequency of approximately 200 Hertz. The initial application of energy is then made to the tip 15. The induced temperature of the tip is then measured, and the sampling is made. The software allows the system to continually cycle so as to minimize the rate at which the error temperature is changing, so that the next voltage value to be sent to the catheter tip 15 can be calculated. The key control equation can be derived from several methods. The system can be formally analyzed to evaluate the coefficients in the control equation or the system coefficients can be determined experimentally. This system has been modeled and was found to be a first order system with the following equation.

Temperature=(A* voltage) * (1-exp(−1*t/tau)) where temperature is the tip 15 temperature, A is a coefficient, t is an arbitary time (usually the average cycle time), and tau is the time constant of the system.

The control system equation is based on the error temperature, i.e. the difference between the desired temperature and the actual temperature. When the tip 15 is actually hotter than the desired temperature, the error temperature has a negative value. The equation is as follows:

$$ET = \text{Desired Temperature} - \text{Actual Temperature}$$

where ET is the error temperature. ET is then used to compute a new voltage value to be sent to the catheter tip 15 by the following equation:

$$V = VO + ET*KI + DET*K2$$

In this equation V is the value to be sent by the power supply 44 to the catheter tip 15, VO is the voltage value sent to the catheter tip 15 on the lat cycle, ET is error temperature, K1 and K2 are experimentally derived constants, and DET is the first derivative of the error temperature with respect to time.

Proper determination of the coefficients K1 and K2 by iterative, mathematical or combined methods allow the catheter tip 15 temperature to be controlled to a precise level. After this value is calculated, it is sent over the interface bus 42 to the power supply 44 and the power supply 44 sends this voltage to the distal end 52 of the catheter assembly 8. Once the desired tip 15 temperature is achieved, the catheter 8 is moved forward through the build-up. The temperature is continually monitored and regulated in this fashion until the plaque 30 is vaporized.

The software is designed to provide an overdamping function at the tip so no temperature overshoot occurs. The computer 40 also allows for estimation of the energy transferred to the plaque 30 and provides data in the event of muscularis 34 damage so the system can be automatically shut off. The thermal compensation circuit 48 eliminates the need for an ice bath, which has been used in the prior art to provide a reference temperature for the thermocouple.

In use, the catheter body 10 is inserted directly inside an artery 28 following the guide wire 16 until the catheter tip 15 reaches the blockage of atherosclerotic plaque 30. It is essential that this catheter assembly 8 be constructed so that it is capable of miniaturization for use within an artery (1.0–3.5 mm in diameter). Direct current and stable voltage are applied as determined by the minicomputer 40, and the catheter tip 15 is used to thermally ablate vessels by direct contact with the cap 14. The thermocouple evaluates the temperature of the catheter tip 15 and brings it to its proper temperature by a feedback system using the temperature compensation circuit 48 and compute control. Specifically, the measured temperature is fed into a control algorithm which determines the next appropriate voltage to be sent out to the catheter tip 15 so that the proper tip 15 temperature can be maintained at all times. The software also provides fall-safe type parameters such that automatic shut-off at the tip 15 can occur in any emergent situation.

Additionally, the feedback data gives some indication of which layer of the arterial wall the angioplasty is affecting based upon the thermal characteristics of the surrounding tissue. This provides a significantly lower perforation rate than has been found in conventional angioplasty. devices. Studies published in the literature show a varying thermal resistance of the three layers of the arterial wall. The muscularis 34 is the layer most resistant to damage by thermal energy. Conversely, atherosclerotic plaque 30 melts at a temperature level lower than that which damages the muscularis 34. The hot tip catheter assembly 8 and its control system take advantage of this natural variation of thermal resistance by maintaining the tip 15 temperature at a level above the needed to melt the plaque 30 but below that which damages the muscularis 34. Thus, the catheter tip 15 is heated to a range of 160° to 180° C. The heat is applied to the plaque 30 for time periods of approximately 30 to 60 seconds in order to resolve the atheromatous buildup. The non-adhesive coating 25 of the tip 15 reduces drag upon the catheter body 10 as it is passed through the vessel and across the area of stenosis. It also inhibits the adhesion of char and tissue debris to the catheter tip 15, which has limited the application of prior thermal angioplasty devices.

The catheter tip 15 has a very low thermal mass, and as it is not heated to an excessive temperature, it does not require complicated cooling mechanisms which have been limitations of prior thermal systems. The tip 15 may be cooled by hypothermic saline which can be injected through the guide wire opening 17, and additionally by losing heat to the surrounding tissues by direct thermal contact. The low thermal mass is also significant in that selective heating of the outer edge of the tip 15 is not necessary, as has been the case in other conventional catheter devices. Further, the catheter tip 15 is designed to be able to remove atherosclerotic plaque buildup 30 and open arteries de novo without the use of a guide wire 16 if a vessel is completely occluded, and can completely open these arteries without need for subsequent balloon angioplasty catheters. The restenosis rate is possibly lessened in this manner.

The hot tip catheter assembly 8 has also taken problems of electrical current into account. In the preferred embodiment, the current flow into the catheter follows a wire to the distal end 52 where it is welded to the semiconductor package 38 itself. The positive power lead 22b is welded completely within the catheter sheath 11 so that the higher voltage is not exposed to any of the tissue. The negative lead 22a is welded to the exterior part of the probe and is coated with a thermally conductive but electrically resistive material. Animal studies conducted with the hot tip catheter assembly 8 revealed no difficulties in that none of the animals suffered any damage from electric shock. Studies were also done in saline to determine the current leakage, and these were all less than 3 milliamperes.

Initial catheter testing has shown the diode package to withstand a maximum temperature of 384° C. on repeated temperature cycles without any failures. Prototype studies done in air showed the catheter could cause cutting of animal protein tissues. These studies were continued using atherosclerotic fresh cadaveric human aorta and they revealed preferential cutting of soft atheromatous plaque with sparing of the muscularis. The experimental results were compared to those published in the literature and revealed comparable degrees of cutting, temperature ranges and power usages. A catheter prototype was then constructed for use in vivo in a rabbit model. This raised the question of arrhythmogenicity from current leakage from the catheter tip. Experiments on the prototype catheters done in saline solution showed a maximum current leakage of 3 milliamperes. Mechanical angioplasty with no heating of the tip was performed during the animal studies and it revealed no plaque removal. In contrast, during in vivo angioplasty of rabbit aorta, iliac, and femoral arteries with the tip temperature at 168° C., angiograms and histologic slides revealed striking plaque removal with no damage to the muscularis. Recent studies with laser type thermal ablation catheters have suggested that mechanical angioplasty caused by direct pressure of the laser was responsible for much of the effect of the device, which resulted in high complication rates. The problem is obviated by a temperature-regulated semiconductor thermal ablation catheter such as is embodied in the present invention.

Figure 6:
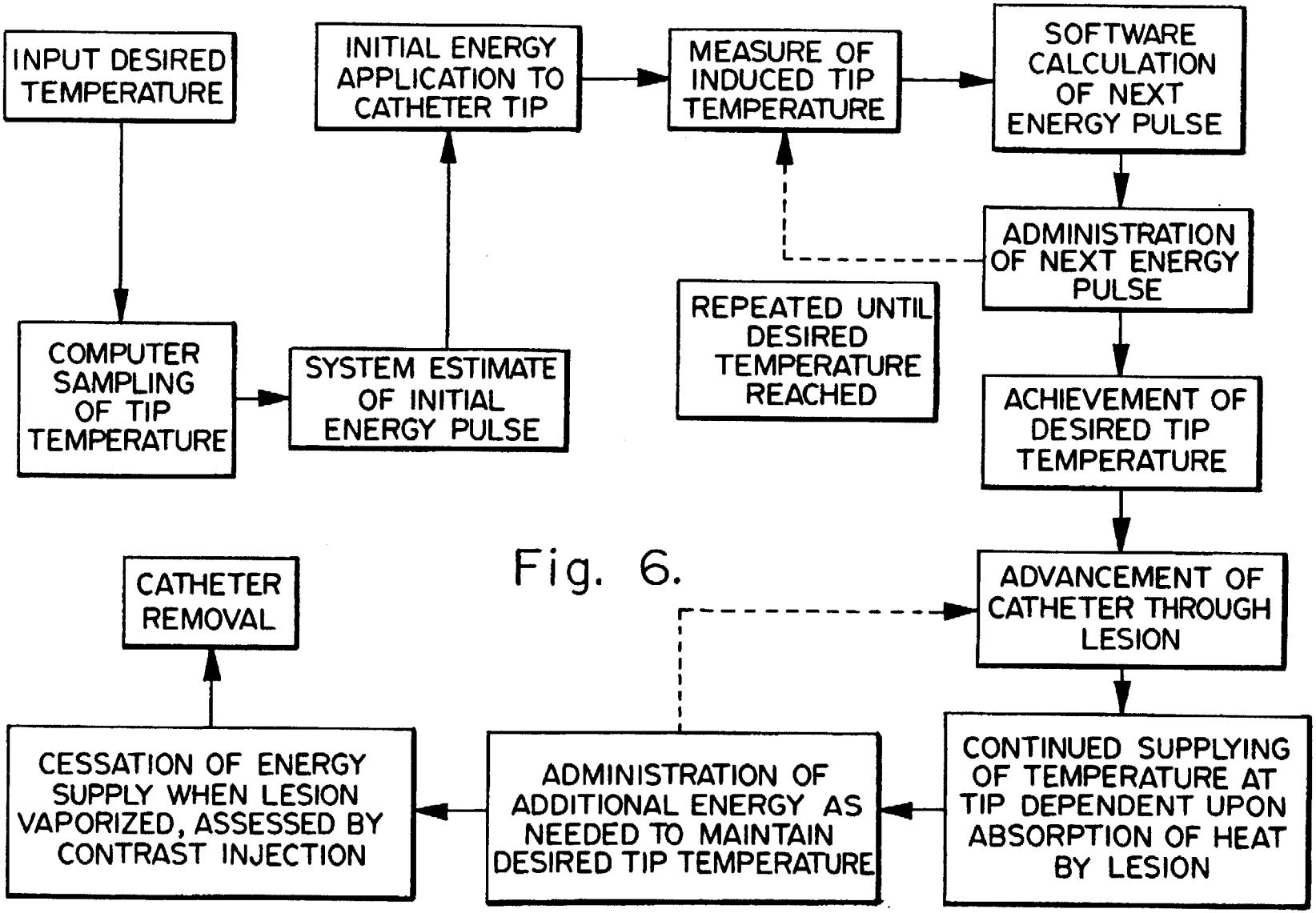
FIG. 6 is a flow diagram of the microcomputer temperature control assembly which regulates the hot tip catheter.
Figure 7:
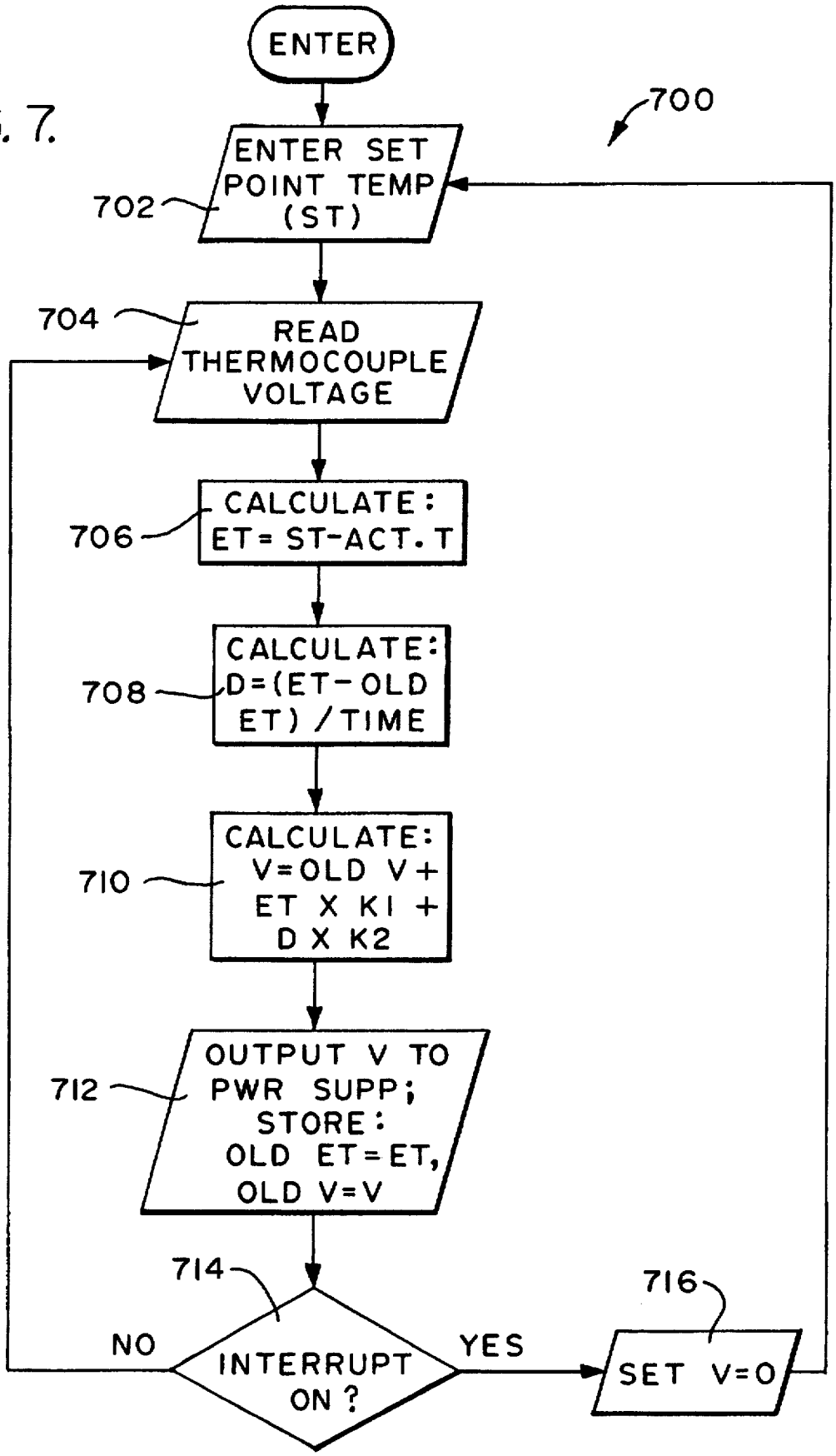
FIG. 7 is a computer program flowchart for operating the microcomputer of FIG. 5 in accordance with the flow diagram of FIG. 6.

FIG. 7 is a computer program flowchart 700 illustrating the operation of micro-computer 40 in accordance with the temperature control flow diagram of FIG. 6. The program enters at step 702 at which the set point temperature, that is, desired temperature is entered into microprocessor 40.

The program then moves to step 704 which reads the thermocouple voltage as provided by leads 20 and converts this voltage to an equivalent temperature. Step 706 then calculates the error temperature (ET) as the difference between the set point temperature (ST) and the actual temperature (ACT T) as indicated by the thermocouple voltage.

In step 708, the program calculates the first derivative (D) of the change in the air temperature since the last reading. This is determined by calculating the difference between the error temperature (as calculated in step 706) and the old error temperature (OLD ET) of the previous pass through the program, divided by the elapsed time since the previous calculation.

Step 710 then uses this information to calculate a new output voltage (V) to be supplied by power supply 44 to heater element 12. New output voltage is determined by adding the old output voltage (OLD V), the error temperature times constant (K1), and the derivative times constant (K2). Constants K1 and K2 are selected in an iterative fashion from air and saline tests to determine the desired response characteristics. Small values for K1 and K2 lead to slow, system response times and large values lead to fast response times resulting in overshoot of the set point temperature. The final values for these constants depend upon the responses desired by the attending physician for the particular application.

In step 712, microprocessor 40 prompts power supply 44 to supply an output voltage V as determined in step 710. This step also stores old error temperature and old voltage respectively equal to current error temperature and output voltage for use in the next set of calculations.

Step 714 then asks whether an interrupt or reset signal is being received by microprocessor 40 which occurs, for example, when a new set point temperature is being entered. If the answer in step 714 is no, the program loops back to step 704. If the answer is yes, the program moves to step 716 which sets the output voltage at zero and then loops back to step 702 to receive the new set point temperature.

Those skilled in the art will appreciate from the discussion above that the present invention provides for very precise control of catheter temperature. This is achieved by controlling the voltage transmitted to heater element 12 in a manner which monitors the slope of temperature change in terms of the error deviation. In this way, deleterious overshooting of the set point is eliminated thereby preventing heat damage to vessel walls which has been a problem in the prior art while, at the same time, precisely controlling temperature at the desired set point to ensure maximum effectiveness in removing plaque.

Those skilled in the art will also appreciate that the present invention can also be used as an intravascular cautery device to occlude side branches of a vessel from inside the vessel, and can be configured for use through the ports of conventional fiberoptic endoscopes and bronchoscopies and the like for cauterization of vessels or to thermally coagulate and resect tumors.

It is to be understood that while certain forms of this invention have been illustrated and described, it is not limited thereto, except in so far as such limitations are included in the following claims.

We claim:

1. A method of applying heat to the interior of a vessel in vivo, said method comprising the steps of:

inserting an electrically heatable, voltage responsive, hot tip catheter assembly having a catheter tip into the vessel;

positioning said catheter tip in the vicinity of the vessel interior to be heated;

heating said catheter tip;

monitoring the temperature of said catheter tip;

comparing said temperature with a set point temperature representative of a predetermined temperature set point for said catheter tip;

determining the deviation between tip temperature and set point temperature;

determining the rate of change of said deviation; and applying a voltage to said catheter tip in accordance with both said deviation and said rate of change of said deviation in order to control the temperature of said catheter tip at said set point temperature.

2. The method as set forth in claim 1, further including the step of applying said voltage to at least one avalanche diode as part of said catheter assembly for heating thereof.

3. The method as set forth in claim 2, further including the step of applying said voltage to three avalanche diodes connected in series.

4. The method as set forth in claim 1, further including the step of providing a thermocouple for monitoring said tip temperature.

5. The method as set forth in claim 1, further including the step of providing a microcomputer as means for performing said monitoring, comparing and determining steps.

6. An apparatus for applying heat to the interior of a vessel in vivo, said apparatus comprising:

an electrically heatable, voltage responsive, hot tip catheter assembly having a catheter tip configured for insertion into the vessel and for positioning of said catheter tip in the vicinity of the vessel interior to be heated said assembly including means for heating said catheter tip; and heat control means operably coupled with said catheter assembly for controlably heating said catheter tip, said control means including means for monitoring the temperature of said catheter tip;

means for comparing said temperature with a set point temperature representative of a predetermined temperature set point for said catheter tip;

means for determining the deviation between tip temperature and set point temperature and for determining the rate of change of said deviation; and means for applying a voltage to said catheter tip in accordance with both said deviation and said rate of change of said deviation in order to control the temperature of said catheter tip at said set point temperature.

7. The apparatus as set forth in claim 6, said catheter tip including at least one avalanche diode responsive to the application of said voltage for producing heat.

8. The apparatus as set forth in claim 7, said catheter tip including three of said avalanche diodes connected in series.

9. The apparatus as set forth in claim 6, said temperature monitoring means including a thermocouple.

10. The apparatus as set forth in claim 6, said control means including a microcomputer.

*11. A method for applying energy to heat tissue comprising the steps of*

*locating a catheter with an energy applying element next to tissue,*

*applying energy to the element while monitoring the temperature of the element,*

*comparing the monitored temperature of the element with a selected temperature,*

*determining the deviation between the monitored temperature of the element and the selected temperature,*

*determining the change of the deviation over time, and*

*applying energy to the element in response to both the deviation and the change of the deviation over time.*

*12. A method according to claim 11*

*and further including the step of providing a thermocouple for monitoring the temperature of the element.*

*13. A method according to claim 11*

*using a computer to perform the steps of determining the deviation and the change of the deviation over time.*

*14. A system for applying energy to heat tissue comprising*

*a catheter with an energy applying element,*

*a source of energy for the element,*

*a temperature sensor associated with the element,*

*processing means operatively connected to the temperature sensor for deriving (i) the deviation between the temperature sensed by the temperature and a selected temperature and (ii) the change of the deviation over time, and*

*control means operatively connecting the energy source and the catheter element for applying energy from the source to the catheter element in response to both the deviation and the change of the deviation over time derived by the processing means.*

*15. A system according to claim 14*

*wherein the temperature sensor comprises a thermocouple carried by the catheter.*

*16. A system according to claim 15*

*wherein the energy applying element comprises a heat-transferring member.*

*17. A system according to claim 16*

*wherein the heat-transferring member comprising at least one avalanche diode responsive to the application of voltage for producing heat.*

*18. A system according to claim 17*

*wherein the temperature sensor comprises a thermocouple.*

*19. A system according to claim 14*

*wherein the processing means includes a computer.*

*20. A system according to claim 14*

*wherein the catheter includes a distal tip, and*

*wherein the energy applying element is carried adjacent the distal tip.*

*21. A system according to claim 20*

*wherein the energy applying element comprises a heat-transferring memeber.*

*22. A system according to claim 21*

*wherein the heat-transferring member comprises at least one avalanche diode responsive to the application of voltage for producing heat.*

*23. A system according to claim 21*

*wherein the temperature sensor includes a thermocouple.*

*24. An apparatus for use in association with a catheter having an energy applying element and a temperature sensor associated with the element, the apparatus being operable for applying energy to the energy applying element, comprising*

*a source of energy for the catheter element,*

*first means operative, when connected with the temperature sensor, for registering temperature sensed by the temperature sensor,*

*second means for storing a comparison temperature,*

*processing means for comparing the temperature registered by the first means with the comparison temperature for deriving both (i) a deviation between the temperature registered by the first means and the comparison temperature and (ii) the change in the deviation over time, and*

*control means connected to the energy source and the processing means and operative, when connected with the energy applying element, for applying energy from the energy source to the energy applying element in response to both the deviation and the change of the deviation over time derived by the processing means.*

*25. An apparatus according to claim 24*

*wherein the processing means includes a computer.*

* * * * *